United States Patent
Verlaan et al.

(10) Patent No.: US 7,375,089 B2
(45) Date of Patent: May 20, 2008

(54) REHYDRATION COMPOSITION

(75) Inventors: George Verlaan, Wageningen (NL);
Robert Johan Joseph Hageman, Waddinxveen (NL); Rudolf Leonardus Lodewijk Smeets, Venlo (NL)

(73) Assignee: N.V. Nutricia, Zoetermeer (NL)

( * ) Notice: Subject to any disclaimer, the term of this patent is extended or adjusted under 35 U.S.C. 154(b) by 276 days.

(21) Appl. No.: 10/697,428

(22) Filed: Oct. 30, 2003

(65) Prior Publication Data
US 2004/0087518 A1 May 6, 2004

Related U.S. Application Data

(63) Continuation of application No. 09/770,773, filed on Jan. 26, 2001, now abandoned.

(51) Int. Cl.
*A61K 31/715* (2006.01)
*A61K 31/13* (2006.01)

(52) U.S. Cl. .................. 514/27; 514/54; 514/663; 514/23

(58) Field of Classification Search ............... 514/300, 514/23, 51, 249, 561, 565, 562, 458, 456
See application file for complete search history.

(56) References Cited

U.S. PATENT DOCUMENTS

| | | | |
|---|---|---|---|
| 4,312,856 A | 1/1982 | Korduner et al. ............ 424/145 |
| 4,631,189 A * | 12/1986 | Kendall et al. ............ 424/278.1 |
| 5,032,411 A | 7/1991 | Stray-Gundersen ............ 426/74 |
| 5,114,723 A | 5/1992 | Stray-Gundersen ............ 426/74 |
| 5,182,299 A * | 1/1993 | Gullans et al. ............ 514/460 |
| 5,292,538 A * | 3/1994 | Paul et al. .................... 426/74 |
| 5,389,383 A * | 2/1995 | Huth ............................ 424/650 |
| 5,397,786 A | 3/1995 | Simone ........................ 514/300 |
| 5,464,619 A | 11/1995 | Kuznicki et al. ........... 424/195.1 |
| 5,498,408 A | 3/1996 | Oltra et al. ................ 424/78.01 |
| 5,580,856 A * | 12/1996 | Prestrelski et al. ........... 514/21 |
| 6,020,139 A * | 2/2000 | Schwartz et al. ............ 435/7.1 |
| 6,039,987 A * | 3/2000 | Strahl .......................... 426/74 |
| 6,296,892 B1 | 10/2001 | Elseviers et al. ........... 426/653 |
| 6,420,342 B1 * | 7/2002 | Hageman et al. ............ 514/23 |
| 6,455,511 B1 | 9/2002 | Kampinga et al. ........... 514/53 |
| 6,514,973 B1 * | 2/2003 | Buchholz et al. ........... 514/249 |
| 6,544,547 B2 | 4/2003 | Hageman ................... 424/439 |
| 2003/0099722 A1 * | 5/2003 | Baxter ........................ 424/679 |
| 2004/0192615 A1 * | 9/2004 | Hageman ..................... 514/23 |

FOREIGN PATENT DOCUMENTS

| WO | WO 91/12734 | 9/1991 |
|---|---|---|
| WO | WO 91/14435 | 10/1991 |
| WO | WO 98/49906 | 11/1998 |

OTHER PUBLICATIONS

Coombes and Hamilton, "The Effectiveness of Commercially Available Sports Drinks," *Sports Med. 2000*, 29(3):181-209 (2000).

* cited by examiner

*Primary Examiner*—Brian Kwon
(74) *Attorney, Agent, or Firm*—Banner & Witcoff, Ltd.

(57) ABSTRACT

The invention relates to a fluid that can be used for preventing or treating hypohydration and the secondary consequences thereof. The fluid comprises one or more carbohydrates and minerals and is further characterized by a low osmolarity. The invention further relates to the use of such a fluid for medical, dietetic and other applications.

31 Claims, No Drawings

REHYDRATION COMPOSITION

This application is a continuation of U.S. patent application Ser. No. 09/770,773, filed Jan. 26, 2001, now abandoned, the disclosure of which is hereby incorporated herein by reference.

The invention relates to a fluid that can be used for preventing or treating hypohydration and the secondary consequences thereof. The invention further relates to the use of such a fluid for medical dietetic and other applications.

Water is the most abundant component of the human and animal body. In vivo, it is the medium in which most biochemical reactions take place. Water homeostasis of the body is therefor of paramount importance. To achieve this, water excretion via the urinary tract and via perspiration (sweating) can be regulated. If a water deficiency arises, the concentration of endogenous compounds such as minerals, glucose, amino acids etc. will rise, which may disturb cellular processes. The total concentration of these compounds, which may be expressed as the osmotic value, can be regulated by selective excretion of some of these compounds from the cell or even from the body.

Furthermore, water is an important medium for transportation of components and for the dissipation of heat from the core of the body to the surface. Termoregulation is extremely important since most biochemical. processes in the body are temperature dependent, e.g. due to enzymatic activity. A rise in temperature in the body will mostly be counteracted by sweating and the induction of feelings of fatigue.

Hypohydration of humans and animals is a much occurring phenomenon that can cause mechanical and chemical damage to tissue, as endogenous compounds, such as minerals, and especially water are lost. This may result in the feelings of physical fatigue. Severe depletion of endogenous compounds, such as glucose, sodium, potassium and water may even disturb the functioning of various organs, such as the liver, heart, pancreas and kidneys, and may be accompanied by feelings of pain, which may persevere even after the dehydration has been reverted to a normal condition of the body.

Hypohydration can arise acutely e.g. as the result of heavy exercise, such as sports or labor, or due to prolonged exposure to conditions of high temperature and humidity. Hypohydration can also be the result of a too low consumption of water over a prolonged period of time. Such a more chronic form of hypohydration, is often developed by the elderly and certain other groups of people, such as long-distance travelers.

Other causes for developing a chronic form of hypohydration include the use of certain components, e.g. drugs, that have a diuretic action and certain clinical or metabolic disorders, such as cystic fibrous, spinal cord injuries, coma and diarrhea. Patients may also suffer from hypohydration before or after surgery. Loss of water may lead to a range of secondary complications, in particular loss of water by persons who suffer from a cardiac condition or a kidney dysfunction.

A loss of water of more than 1% of the body weight is generally considered as leading to water deficiency, wherein biochemical processes in the cells, the functioning of organs and tissues and the performance of the subject may become imparted. A decrease in the water content may result in a decrease in blood plasma volume, which leads to a decrease in the cardiac output (stroke volume). This will cause a reduction in the blood supply to tissues and organs, which in turn has a bad impact on the performance thereof. The reduction of blood volume will also impart the dissipation of heat from the core of the body to the skin, where the heat could be dissipated to the environment.

Many drinks have been developed to supply lost water and minerals to the body, most of which aim at the maintenance of the water homeostasis during sports activities. These drinks typically comprise small carbohydrates, proteins and/or amino acids, minerals and several other components. Several drinks are reviewed by Co mbes in "Sports Med 2000; 29(3), 181-209.

"Red Bull" is a hypertonic sports energy drink, comprising per 8.3 fl. oz. (about 250 ml) 28 g carbohydrates (sucrose and glucose), 215 mg sodium (as taurate), about 0.4% taurine, about 0.032% caffeine and less than 0.03% inositol. It further comprises some vitamins, niacin and less than 0.4% glucuronolactone. Red Bull has a very high energy content, mainly in the form of free sugars (mono- and disaccharides), which may be undesirably for dietary reasons.

"Isostar" is a energy drink comprising 15 g/l maltodextrines and 61 g/l sucrose. It has a relatively high fructose content (fructose to glucose ratio is approximately 0.67. The product further comprises 180 mg/l potassium, 690 mg/l sodium and unknown amounts of calcium, magnesium and several vitamins. Like "Red Bull" Isostar has a high level of free sugars.

A new variety of Isostar comprises 68 g of carbohydrates (66 g sucrose), only one type of metal ion (sodium), some vitamins and an uactivator complex", i.e. a mixture of taurine, caffeine, inositol tyrosine and phenylalanine. The presence of the latter makes this drink unsuitable for administration to patients suffering from PKU (phenylketonurea).

In addition to several sport drinks, some "Oral Rehydration. Solutions" have developed, which are typically prescribed on medical indication, e.g. after a period of diarrhoea. A well-known example of such a compound is "Oriserl by Nutricia, which comprises 19.8 g/l glucose, 1.9 g/l citrate, 2.1 g/l sodium, 0.8 g/l potassium and 2.9 g/l chloride.

In WO 94-15488 a rehydration composition is disclosed. The concentrations of the individual constituents of the composition are not disclosed, nor is any reference made to the importance of the tonicity of the serving unit, by which the composition is administered. From the description, it may be concluded that the composition is hypertonic. A serving unit of the composition comprises up to 100 g of at least one carbohydrate, 2-2500 mg of at least one electrolyte, ammonia neutralizer(s) (e.g. aspartate, arginine, glutamate), energy enhancer(s) (e.g. branched chain amino acids, carnitin, choline, creatine), antioxidant(s), 1-30 mg of one or more "membrane stablizers" (e.g. choline, betaine or methionine) and a neuromuscular function enhancer (e.g. octacosanol). Such a composition is relatively complex (e.g. containing 30 different components) and expensive to make. A composition with a high energy content is shown to solve dehydration complaints better than a composition with a lower energy content. The abundance of relatively high levels of amino acids and other nitrogen sources are undesirable for many subjects who already have a nitrogen rich diet and for subjects who must take care not to digest to much nitrogen (e.g. patients suffering from kidney. disorders). Hence the use of an "ammonia neutralizer" is necessary to avoid metabolic problems.

In WO 91/12734 a beverage is disclosed that may be used to replenish water and to provide an energy source. The beverage comprises 3-50 mEq/l electrolytes, 0-8wt % carbohydrates, up to 14% of a sweetener and an edible acid. The beverage has an osmolality of 100-270 mOsm/l. The fructose to glucose ratio is very high. Fructose in sports drinks has been reported to be a potential cause of diarrhea. Diarrhea is not only discomforting but also gives rise to extra dehydration.

WO 98/49906 deals with a product for pre-operative use, comprising a daily dose of 5-130 g soluble carbohydrates and 1-30 g glutamin or equivalents. For reasons discussed above, high levels glutamin may be undesired because of the nitrogen content. The product may comprise N-acetylcystein, vitamin B6, zinc and magnesium. The osmolarity may be up to 450 mOs/l WO 91/14435 discloses a method for treating osmotic disturbances such as hypernatremia and hyponatremia by administration of an organic osmolyte such as a polyol, e.g. creatine or inositol certain amino acids choline, betaine, or precursors thereof. The usefulness of consuming these components was suggested from measuring the rise in concentrations of said components in adrenal medulla or the brain after consumption of meals with a high sodium level or after dehydration, without compensation for cell volume. Effects for betaine or glycerol were not demonstrated, nor is the use of mineral or other supplements mentioned.

Known compositions to treat dehydration are usually hypertonic and their activity is mainly directed to the restoration of the water content, often in combination with the administration of high levels of compounds that are a fast energy source. Little or no attention is paid to the rate of gastric emptying of the product or to secondary effects such as the protection of tissue and organs against possible detrimental effects on their functioning and the levels of endogenous compounds such as minerals, amines and glucose in certain physiological systems (e.g. blood) of the body.

It is an object of the present invention to provide a fluid that after administration contributes to the prevention from disturbances in water, to homeostasis and to a rapid restoration of the bodily water content after dehydration. It is further an object to provide a fluid that can be effective in the protection against secondary effects of hypohydration and to provide a fluid that does not give rise to a high level of undesired side effects.

Accordingly, the present invention relates to a hypotonic fluid for preventing or treating hypohydration, comprising a methyl amine and/or a flavanolignan, said fluid further comprising one or more digestible carbohydrates and one or more minerals, wherein said fluid has an essentially hypotonic osmolarity.

Osmolarity as used herein is to be understood as the number of dissolved components per liter. 1 Osm/l means 1 mole of dissolved components per liter.

Tonicity is a measure for the osmotic pressure (the pressure as a result of the presence of dissolved particles) relative to the osmotic pressure of the blood fluids of a subject.

Hypotonic as used herein means to have a osmotic pressure lower than the osmotic pressure of the blood fluids of the person to be treated.

Isotonic is used to indicated a fluid having the same osmolarity as the blood fluids (typically 280-310 mOsm/l).

Hypohydration is a condition wherein the content of bodily water is too low. It may for example be caused by extensive loss of water or by insufficient intake of water. The process leading to hypohydration is referred to as dehydration.

The term digestible carbohydrates is used herein to indicate a carbohydrate of which at least 60% are physiologically digestible by the enzymes as they occur in the gastrointestinal tract of the species to be treated.

The term oligosaccharide is used to indicate, a carbohydrate having three to 19 monosaccharide units. The term polysaccharide is used to indicate a molecule containing more than 19 monosaccharide units. When referred to the presence of a specific monosaccharide, this should be interpreted as the presence of said specific monosaccharide as a free monosaccharide or as a part of a di, oligo- or polysaccharide unless stated otherwise.

The term subject is used to describe any living animal to which a fluid according to the invention can be administered, including humans, mammals, birds, reptiles and other animals.

It has been found that a fluid according to the invention is very effective in preventing and/or treating the loss of bodily water in humans and/or animals. A fluid according to the invention has been found to improve the speed and efficiency of water absorption by the body. The invention further provides a fluid that has been found to be very effective in helping the body to maintain glucose and mineral homeostasis and may contribute to the reduction of negative side-effects that are associated with a disturbance in the homeostasis of water, minerals, glucose and/or other endogenous compounds. A fluid may for example have a modulating effect on the insulin response, which helps to maintain or restore the glucose balance in the blood plasma. A fluid may also reduce the risk of diarrhea as a result of the intake of high volumes of drinks, e.g. during endurance sports, such as long distance running or cycling. A fluid according to the invention has also been found to reduce the risk for developing muscle cramps as a result of dehydration, e.g. during or after heavy exercise.

A fluid according to the invention can be used for the treatment or prophylaxis of any type of dehydration in healthy or ill subjects, including water loss due to excessive sweating (heavy labor, sports, prolonged exposure to a hot environment, e.g. a humid hot environment), water loss due to diarrhea or due to the effects of diuretic drugs or too low water consumption (e.g. during long-distance traveling, elderly, hospital patients who stay long in bed and are staying in a warm environment, patients in a coma).

Preferably the fluid, when ready for administration, has an osmolarity of 300 mOsm/l or less, more preferably an osmolarity of less than 280 mOsm/l Very good results have been achieved with a fluid having a osmolarity in the range of 70 to 275 mOsm/l.

It has been found that a low osmotic pressure has a beneficial effect on the speed of water-uptake. In general, a low osmolarity is achieved by using a fluid with a dry mass content of 9 wt. % or less, e.g. 5%.

A fluid with a digestible carbohydrate amount of 10-80 g/l has been found to be very effective. The water-uptake after ingestion of such a fluid has been found to be very fast. Preferably the digestible carbohydrate amount is 20-75 g/l and more preferably 26-65 g/l. Carbohydrates are an energy source, but it has also been found that a digestible carbohydrate promotes, the water absorption by the body.

At least a part of the digestible carbohydrates may be present in the form of oligosaccharides and/or polysaccharides. A fluid comprising oligo and/or polysaccharide material is faster transferred from the stomach to the intestines than a conventional fluid in which the carbohydrate content is mainly) in the form of mono- and disaccharides Thus a faster water uptake is promoted. Preferably the composition comprises very little sucrose, e.g. less than 1 g/l, preferably less than 0.5 g/l, most preferably the composition is essentially free of sucrose.

Particularly, suitable carbohydrates have been found to be polysaccharides comprising glucose. Preferably at least one carbohydrate, such as a maltodextrin, is present which has an average chain length in the range of 3-50 monosaccharide units. Maltodextrin is a particularly preferred carbohydrate. A maltodextrin fraction with a dextrose equivalent (DE) in the range of 4-30, preferably 6-25 has been found to be particularly effective. (A DE of 1 indicates a totally non-hydrolyzed maltodextrin, a DE of 100 a fully hydrolyzed maltodextrine.) Apart from the use of maltodextrin to improve the anti-dehydrative effect of the product, it is also possible to alter the taste of the product by adding a maltodextrin with a different DE. A higher DE results in a sweeter product. It has been found that under most physiological conditions the rate of glucose uptake is not largely affected by varying the DE of the maltodextrin, since the speed of digestion of the maltodextrin is not the limiting step in the uptake of glucose into the blood plasma.

A fluid wherein at least 50 wt. %, preferably at least 75 wt. % of the carbohydrate content is in the form of a polysaccharide has been found to be very effective for the prevention and/or treatment of hypohydration. It has also been found that such a fluid can be administered with decreased risk for causing hypoglucaemia.

Glucose, inositol, ribose, galactose and mannose moieties have been found to be stimulating the rate of water absorption by the body very effectively. Inositol and especially glucose are preferred.

A much preferred fluid comprises more than one type of monosaccharide units. In particular, the presence of one or more carbohydrates comprising glucose and at least one other monosaccharide unit chosen from the group of fructose, ribose, galactose, mannose and inositol has been found to have a positive effect on the water uptake by the body and the glucose metabolism (such as a rapid increase of the glucose level in blood plasma). These two aspects may be further improved in a fluid comprising more than two, preferably more than three different types of monosaccharide units. The variety in monosaccharide units is believed to promote the water uptake rate and to support the mineral homeostasis. In a preferred embodiment the ratio of fructose and mannose to glucose is 0.05-0.6 ((mole fructose+mole mannose)/mole glucose), more preferably 0.1-0.2. For reasons of taste, the lactose content is preferably present in a concentration between 0 and 60 wt % of the total digestible carbohydrate content.

In another preferred embodiment ribose, galactose and/or inositol are present in an amount of at least 0.5 g/l. Inositol may be present as the pure compound, e.g. as myo-inositol. Galactose, ribose or mannose may be present as a free monosaccharide and/or as part of one or more di-, oligo- and/or polysaccharides. Ribose in an embodiment of the invention is preferably synthetic.

A saccharide may be present in any isomeric form. Preferably at least part of the saccharide is present in the physiologically active D-form or as a racemate.

Preferred methylamines are dimlethylglycine, choline, sarcosine and betaine. Betaine is particularly preferred. The methyl amine may a natural or synthesized methyl amine. A particularly suitable natural source for betaine is a betaine-rich extracts from a natural source such as sugar beet. The methyl amine concentration is preferably between 0.1 and 20 g/l, more preferably 0.2-10 g/l. The methyl amine may be present as base or as salt. Preferred methyl amine salts include the phosphate and chloride salts and mixtures thereof.

Examples of suitable flavanolignans include silibin, silydianine, silychristine, silandrin and silyhermin. Such a flavanolignan can be made synthetically or extracted from plant material. Extraction can for example be performed by slurrying a plant material in a polar solvent, filtrating the slurry and purifying the filtrate. A fluid according to the invention preferably comprises 0.1-8 g flavanolignans. Silibin is a particularly preferred flavanolignan. It is commercially available and can be made synthetically or extracted from a natural source. For example, *Silybum marianum* (milk thistle), and particularly the fruit thereof, is rich in silibin and other flavanolignans. A known commercially available milk thistle extract comprising silibin is silymarin. In a preferred embodiment, a fluid according to the invention comprises silymarin as a source of silibin or an extract that has been standardized on silymarin, in particular those that are normalized on 70% analogy to silymarin. It is found that silymarin or an analogous extract in a fluid according to the invention protects body cells against dehydrating conditions. This can be a very important aspect of the silymarin activity, not only for administration to subjects suffering from a medical disorder but also for healthy subjects, since especially during heavy exercise the immune system may be detrimentally affected. Preferably a fluid according to the invention comprises 0.2-10 g/l silymarin, providing approximately 0.1-8 g silibin. Silibin may also be extracted from any other plant material such as from sugar beet.

Minerals (inorganic anions and inorganic cations) are preferably present in a total concentration of 0.1-30 g/l, more preferably 1-20 g/l, most preferably 1.5 to 15 g/l. Any food grade salt may be used as a mineral source. Preferred minerals include sodium, potassium, chloride, phosphate, magnesiurm, zinc, calcium, iron and copper, which may or may not be present in any combination and concentration within the indicated ranges and their solubilities.

Suitable sources for sodium, zinc, iron, magnesium, calcium and potassium include salts thereof with chloride, phosphates and with organic acid residues, like citrate, malate or pyruvate. Suitable sources for chloride include their salts with sodium, potassium, zinc, magnesium, calcium, iron and arginine hydrochloride. In particular for applications wherein large volumes are ingested, it is preferred to not to use a salt of sulfate, because high amounts of sulfate may cause unwanted physiological effects.

In one embodiment the total mineral content essentially consists of sodium, potassium and chloride. Very good results have also been achieved with a fluid comprising, at least 100 mg/l magnesium, at least 10 mg/l zinc, at least 300 mg/l calcium, at least 5 mg/l iron, or a combination thereof.

For certain applications, such as a fluid for use during endurance sports, it may be desired the fluid has a relatively low potassium concentration. During endurance sports the glucose levels in the blood may drop and the potassium levels may rise, due to the release of intracellular potassium. An extra high potassium intake may not be desired in such a case, because it may increase the risk of cramp. Accordingly it is conceived that for such applications specific fluids may be prepared in which smaller amounts of potassium are included. It has been found that a high level of calcium and/or magnesium reduces the risk for cramp in such an application.

The presence of one ore more minerals in a fluid according to the invention has been found to be particularly advantageous for administration to animals or humans that regularly experience heavy exercise (or are going to experience heavy exercise) and for subjects who are deficient in said mineral(s).

In order not to overexpose the body to nitrogen, the content of nitrogen is preferably not higher than 3 g/l, more preferably not higher than 2 g/l. A fluid is preferably essentially free of proteins. This may be desirable for subjects who are on a nitrogen low diet or patients suffering from PKU. It has also been found that the transfer-rate of a substantially protein-free fluid from the stomach to the gut is improved, which results in an accelerated uptake of water, glucose and minerals from the intestines into the body.

Although the absence of proteins is preferred for many embodiments of the invention, an embodiment such as a dairy whey drink may compris some residual protein. Low amounts of amino acids may be included in some embodiments to achieve specific results that are known to exist for these amino acids. Arginine, for example, may be included in an amount of up to 2 gram per daily dose. Glucose absorption may be enhanced by the presence of small amounts of a specific amino acid, such as methionxine. Such an amino acid may be present in a concentration of 0.1-15 g/l, preferably 0.2-5 g/l, more preferably 0.5-4 g/l.

A fluid according to the invention may further comprise glycerol. glycerol is preferably present in a concentration of 0.1-20 g/l and more preferably in a concentration of 0.2-10 g/l. Glycerol may increase the osmolarity of a body fluid, which helps to retain the water and reduce the excretion of water via urine.

Other possible ingredients of a fluid according to the invention include lipoic acid, one or more vitamins (e.g. tocopherol), malate, citrate, phosphate, taurine, caffeine. Vitamins can be present for various reasons. Some vitamins contribute to metabolic processes, e.g. the energy household, others, such as tocopherol have antioxidative properties, which may help to prevent damage to tissues and organs due to oxidative stress, which often results from heavy exercise.

If present, the concentration is preferably at least 20 mg/l for lipoic acid, preferably 0.2-2 g/l for taurine, preferably 0.1-1g/l for caffeine. A fluid may comprise caffeine from a chemically pure quality or caffeine from a plant material extract, such as an aqueous extract of Guarana (*Paulnia Cupana*). It was found that taurine shows in particular a very positive contribution to the effects of a fluid that is administered for prevention of dehydration.

Preferably a fluid according to the invention comprises no or very low amounts of lipids with long chain fatty acids, i.e. a fatty acid with an aliphatic chain of 18 carbon atoms or more. Medium chain fatty acids, e.g. having 4-14 aliphatic carbon atoms, may be present to an amount providing up to twenty energy percent of the total energy of the fluid. Emulsifier(s) may be present to provide a clear and homogenous fluid.

The pH of a fluid is in the range of 2.5-6.8, preferably of 2.8-4.5, among other reasons because of the desirable palatability that can thus be achieved. The pH may be adjusted within this range by any means acceptable to food products. Preferably phosphoric acid/phosphate, malic acid/malate and/or citric acid/citrate is used for pH adjustment because of their advantageous physiological effects. Phosphate is preferably used to provide a concentration in the fluid of 0-4 g/l, more preferably 0.05-4 g/l and even more preferably 0.1-2 g/l. Citrate is preferably used to provide a concentration in the fluid of 0-4 g/l, more preferably 0.1-4 g/l and even more preferably 0.2-2 g/l. Malate is preferably used to provide a concentration in the fluid of 0-4 g/l, more preferably 0.4-2 g/l. It has been found that in particular within these ranges a rapid restoration of water, mineral and glucose homeostasis can be achieved.

A fluid according to the invention may have any suitable form for administration. Preferred embodiments include a fluid for oral administration such as a fruit juice, a dairy drink (preferably low in proteins and fat), a water 1.9 solution, a beverage and the like. Other embodiments include fluids for tube administration and for enternal administration.

The invention further relates to a concentrate, which itself is not necessarily a hypotoric fluid, that can be used for the preparation of a fluid according to the invention. Such a concentrate typically comprises the ingredients for a hypotonic fluid according to the invention in the proper ratio such that the hypotonic fluid can simply be made by adding the correct amount of a palatable drink, preferably tap water, mineral water or demineralized water. For example a concentrate may comprise 10 g digestible carbohydrate, 0.5 g methylamine(s) (e.g. betaine), 0.1 g glycerol and 0.5 g minerals in a dry powder or as a bar. A hypotonic fluid according to the invention can be prepared by adding the prescribed amount of demineralized water (e.g. 1 l ). A concentrate may also divided into a number of different dosage units each comprising some of the ingredients of a fluid according to the invention, e.g. a concentrate consisting of a dosage unit comprising 60 g of digestible carbohydrates and 2 g betaine in 250 ml water that can be mixed with another dosage unit comprising 1 g silibin, 1 g caffeine and 3 g minerals in 250 ml water to form a fluid according to the invention.

A concentrate may for example have the form of a pre-mix, a powder, an agglomerate, a fluid, a syrup, a gel, a tablet or a capsule. Another aspect of the invention is a method for manufacturing a concentrate for the preparation of a fluid, said fluid comprising betaine, one or more digestible carbohydrates and one or more minerals, wherein said fluid has an essentially hypotonic osmolarity, for preventing or treating hypohydration.

The invention further relates to a fluid according to the invention for medical use, to the use of betaine and/or silibin in a hypotonic fluid to provide improved prevention against hypohydration and to the use of betaine and/or silibin in a hypotonic fluid to provide improved recovery from hypohydration.

The invention further relates to a method for treating or preventing hypohydration, comprising the administration of a fluid according to the invention. The invention has found to be effective to treat low to moderate water loss but also to treat a high water loss of 4% of the body weight. The amount of fluid that is preferably administered per dosage will depend upon the purpose (prevention or treatment) the physical condition of the subject, the actual degree of water loss, and the medical condition (e.g. diarrhoea). The concentrations of the active ingredients may also be varied depending upon these factors and possibly the depletion of other components, such as certain minerals. The recommended maximum daily dose of certain compounds to be administered via a fluid according to the invention may also be taken into account. Examples of suitable recommended daily doses for some of the compounds that may be present in a fluid according to the invention are 0.14-4.5 g, preferably 0.15-3 g digestible carbohydrate/kg bodyweight/day; 0.2-20 g day betaine and max. 2 g/day for arginine. It is stressed that these figures are indications only and may be altered within the scope of the invention. The skilled professional will be able to deduct a suitable dose from the factors mentioned before.

The fluid is preferably administered orally. The invention does however also cover a method for enteral or tube administration. Naturally for such an application the used ingredients should be medical grade.

Of the medical applications, a method according to the invention has been found to be particularly suitable for a subject suffering from a gut disorder, cystic fibrosis, a cardiovascular disease and symptomatically or physiologically related disorders.

A method according to the invention may also be of use before, during or after surgery of a subject. It has been found that such patients often suffer from the risk of dehydration. They are often exposed to a warm environment, while they are not able to drink. Also elderly people may successfully be treated with a method according to the invention. Dehydration in elderly is often caused by the combination of living in a warm environment and an often observed tendency to forget to drink regularly.

The invention also relates to a method for the prevention or treatment of dehydration of subjects who are exposed to high temperatures, and/or physical exercise, including labor and sport by administration of a fluid according to the invention to a subject before, during or after being exposed to said circumstance.

It is also an aspect of the invention to provide a method for manufacturing a fluid, comprising betaine, one or more digestible carbohydrates and one or more minerals, wherein said fluid has an essentially hypotonic osmolarity for preventing or treating hypohydration.

The invention will now further be elucidated by the following nonlimiting examples.

EXAMPLE 1

Sportsdrinks

| per serving of 567 ml is included | |
|---|---|
| glucose | 8 g |
| fructose | 6 g |
| maltodextrin | 20 g |
| glycerol | 1.0 g |
| taurine | 1.0 g |
| betaine | 1.0 g |
| Guarana | 0.27 g, providing 0.1 g caffeine |
| Sodium phosphate | 0.5 g |
| Sodium chloride | 0.1 g |
| Potassium citrate | 0.3 g |

These amounts are dissolved in demineralized water to make up 567 ml

EXAMPLE 2

Sportsdrink

| per serving of 567 ml | |
|---|---|
| glucose | 6 g |
| fructose | 0.6 g |
| maltodextrin | 12 g |
| betaine | 1.0 g |
| taurine | 0.1 g |
| L-methionine | 0.1 g |

| -continued | |
|---|---|
| per serving of 567 ml | |
| Ribose | 2 g |
| Inositol | 0.1 g |
| Sodium citrate | 0.2 g |
| Sodium chloride | 0.2 g |
| Calcium malate | 0.2 g |
| Magnesium malate | 0.1 g |

EXAMPLE 3

Drink to Support Persons Suffering from Diarrhea

The following compounds were dissolved in 1 l water:

| glucose | 6 g |
|---|---|
| ribose | 1 g |
| inositol | 0.2 g |
| fructose | 2 g |
| maltodextrine | 5 g |
| betaine | 2 g |
| folic acid | 100 µg |
| Methionine | 0.3 g |
| sodium | 2.1 g |
| potassium | 0.8 g |
| chloride | 2.9 g |
| citrate | 1.9 g |

The invention claimed is:

1. A fluid for treating hypohydration, comprising at least one methyl amine, one or more digestible carbohydrates and one or more minerals, wherein the methyl amine is selected from dimethylglycine and sarcosine with the amount of methyl amine being between 0.2-10 g/l, the digestible carbohydrate is in the amount of between 20-75 g/l, the mineral includes at least one of calcium and magnesium, and said fluid has an essentially hypotonic osmolarity in the range of 70 to 275 mOsm/l, and wherein the fluid treats hypohydration when administered to a subject in need thereof.

2. A fluid according to claim 1, comprising more than two different types of monosaccharide units.

3. A fluid according to claim 1, having a dry mass content of 9 wt. % or less.

4. A fluid according to claim 1, wherein the digestible carbohydrate concentration is between 10 and 80 g/l.

5. A fluid according to claim 1, wherein at least part of the digestible carbohydrates is formed by polysaccharides comprising glucose and wherein at least 0.5 g/l of the digestible carbohydrates is ribose or inositol.

6. A fluid according to claim 1, wherein the one or more carbohydrates have an average chain length in the range of 3-50 monosaccharide units.

7. A fluid according to claim 1, wherein at least 50 wt. % of the carbohydrate content is in the form of one or more of oligosaccharides or polysaccharides.

8. A fluid according to claim 1, wherein the one or more carbohydrates are selected from the group consisting of glucose, fructose, galactose, mannose, ribose and inositol.

9. A fluid according to claim 8, comprising glucose, fructose, and mannose, and wherein fructose and mannose together are present in an amount between 0.05-0.6 mole per mole glucose.

10. A fluid according to claim 1, wherein the one or more carbohydrates comprise at least 0.5 g/l ribose, at least 0.5 g/l inositol and/or at least 0.5 g/l galactose.

11. A fluid according to claim 1, wherein the mineral concentration is between 0.1 and 30 g/l.

12. A fluid according to claim 1, further including one or more minerals selected from the group consisting of sodium, potassium, chloride, phosphate, zinc, iron and copper.

13. A fluid according to claim 1, wherein the magnesium concentration is 100 mg/l or more.

14. A fluid according to claim 12, wherein the zinc concentration is 10 mg/l or more.

15. A fluid according to claim 1, wherein the calcium concentration is 300 mg/l or more.

16. A fluid according to claim 12, wherein the iron concentration is 5 mg/l or more.

17. A fluid according to claim 1, comprising glycerol, lipoic acid, a vitamin, citrate, phosphate, malate, taurine, caffeine or a combination thereof.

18. A fluid according to claim 17, comprising tocopherol.

19. A fluid according to claim 17, wherein glycerol is present in a concentration of 0.1-20 g/l.

20. A fluid according to claim 17, wherein lipoic acid is present in a concentration of at least 20 mg/l.

21. A fluid according to claim 17, wherein taurine is present in a concentration of 0.1-2 g/l and wherein citrate is present in a concentration of 0.2-2 g/l.

22. A fluid according to claim 17, wherein caffeine is present in a concentration of 0.1-1 g/l.

23. A fluid according to claim 1, comprising methionine.

24. A fluid according to claim 1, having a pH in the range of 2.5-6.8.

25. A fluid according to claim 1, having a nitrogen content of less than 3 g/l.

26. A fluid according to claim 1, in the form of a water solution, a fruit juice, a whey dairy drink, a beverage, or a fluid for tube or enteric administration.

27. Concentrate for preparation of a fluid according to claim 1.

28. Concentrate according to claim 27, in the form of a pre-mix, a powder, an agglomerate, a fluid, a syrup, a gel, a tablet or a capsule.

29. A composition according to claim 1,
wherein the one or more minerals are present in an amount between about 1.5 and about 15 g/l,
wherein the one or more carbohydrates are selected from the group consisting of galactose, ribose, inositol and mannose present in a concentration of at least about 0.5 g/l, and
wherein the composition has a nitrogen content of less than about 3 g/l.

30. A composition according to claim 1, wherein the fluid is for treating an ill subject.

31. A composition according to claim 30, wherein the ill subject is a subject suffering from hypohydration selected from the group consisting of a subject that used a drug having a diuretic action, a subject having a spinal cord injury, a subject in a coma, a subject who is confined to bed, and a subject having a kidney dysfunction.

* * * * *